US009592368B2

(12) United States Patent
Wada

(10) Patent No.: US 9,592,368 B2
(45) Date of Patent: Mar. 14, 2017

(54) INTRODUCER SHEATH AND METHOD FOR USING THE SAME

(71) Applicant: TERUMO KABUSHIKI KAISHA, Shibuya-ku, Tokyo (JP)

(72) Inventor: Satoshi Wada, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/864,319

(22) Filed: Sep. 24, 2015

(65) Prior Publication Data

US 2016/0008588 A1      Jan. 14, 2016

Related U.S. Application Data

(63) Continuation of application No. PCT/JP2013/059931, filed on Apr. 1, 2013.

(51) Int. Cl.
*A61M 25/10* (2013.01)
*A61M 25/00* (2006.01)
*A61M 25/06* (2006.01)

(52) U.S. Cl.
CPC ........ *A61M 25/10* (2013.01); *A61M 25/0023* (2013.01); *A61M 25/0662* (2013.01); *A61M 2025/0024* (2013.01); *A61M 2025/1081* (2013.01)

(58) Field of Classification Search
CPC .............. A61M 25/10; A61M 25/0023; A61M 25/0662; A61M 2025/0024; A61M 2025/1081

USPC ........ 600/203, 205, 206, 208, 215; 606/191; 604/96.01, 43
See application file for complete search history.

(56) References Cited

U.S. PATENT DOCUMENTS

| 4,406,656 A | 9/1983 | Hattler et al. |
| 4,601,713 A | 7/1986 | Fuqua |
| 5,997,508 A * | 12/1999 | Lunn ................. A61M 25/0662 604/164.08 |
| 2005/0197624 A1* | 9/2005 | Goodson, IV .... A61M 25/0662 604/96.01 |

(Continued)

FOREIGN PATENT DOCUMENTS

| JP | 1-094863 A | 4/1989 |
| JP | 2008-512196 A | 4/2008 |

(Continued)

OTHER PUBLICATIONS

International Search Report (PCT/ISA/210) mailed on Jun. 18, 2013, by the Japanese Patent Office as the International Searching Authority for International Application No. PCT/JP2013/059931.

(Continued)

*Primary Examiner* — Pedro Philogene
*Assistant Examiner* — David C Comstock
(74) *Attorney, Agent, or Firm* — Buchanan Ingersoll & Rooney PC

(57) ABSTRACT

A primary lumen and a secondary lumen, which is formed so as to be expandable, are formed inside a sheath main body having a deformation portion which is disposed so as to include at least a part of the outer peripheral portion of the sheath main body. The deformation portion is deformed so as to be expanded outwardly in accordance with the expansion of the secondary lumen.

19 Claims, 8 Drawing Sheets

(56) References Cited

U.S. PATENT DOCUMENTS

2006/0135981 A1\*  6/2006  Lenker ............... A61B 17/3439
                                                    606/191
2006/0235457 A1   10/2006  Belson

FOREIGN PATENT DOCUMENTS

| JP | 2008-538709 A | 11/2008 |
|---|---|---|
| WO | WO 2006/031582 A2 | 3/2006 |
| WO | WO 2006/113544 A2 | 10/2006 |

OTHER PUBLICATIONS

Office Action (Decision of Refusal) issued on Sep. 27, 2016, by the Japanese Patent Office in corresponding Japanese Patent Application No. 2015-509705, and an English Translation of the Office Action. (6 pages).

Japanese Official Action mailed Jun. 28, 2016 by the Japanese Patent Office in counterpart Japanese Application No. 2015-509705 with English translation (8 pages).

\* cited by examiner

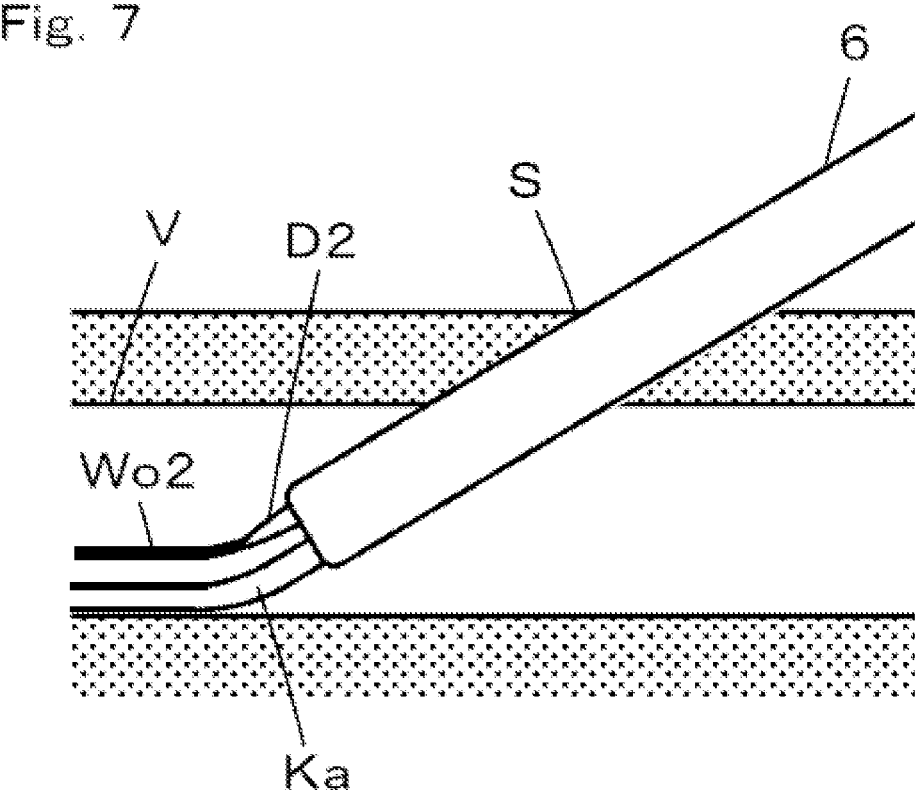

1

INTRODUCER SHEATH AND METHOD FOR USING THE SAME

CROSS-REFERENCE TO RELATED APPLICATION

This application is a continuation of International Application No. PCT/JP2013/059931 filed on Apr. 1, 2013, the entire content of which is incorporated herein by reference.

TECHNICAL FIELD

The invention relates to an introducer sheath and a method for using the same, and more particularly to an introducer sheath for introducing a plurality of catheters into a biological lumen and a method for using the same.

BACKGROUND DISCUSSION

In the medical field, a catheter which can be inserted into a lesion area along a biological lumen, for example, blood vessels, bile ducts, trachea, esophagus, or urethra in order to treat the lesion area generated in the biological lumen has been used. In general, the catheter is introduced into a biological lumen from an approach site which is formed by puncturing a living body. An introducer sheath which internally has a lumen is disposed on the approach site, and a catheter is introduced into a biological lumen through this introducer sheath. Accordingly, it is possible to insert a catheter into a biological lumen without directly causing friction between the catheter and biological tissues when treating a lesion area.

In recent years, the method of treating a lesion area in a biological lumen has become complicated. For example, in some cases, when treating chronic total occlusion (CTO) occurring in a blood vessel or the like, two catheters are simultaneously inserted into the blood vessel from both sides of the lesion area to treat the lesion area by the combined operation of the two catheters. At this time, it is necessary to form approach sites by puncturing two sites in order to insert the two catheters into the blood vessel and this has become a great burden on a person to be treated.

For example, JP-A-1-94863 discloses a catheter introducer for simultaneously inserting a plurality of catheters into a biological lumen from one approach site. The catheter introducer has one introducer sheath and a plurality of hubs which communicate with a lumen of the introducer sheath through an introduction passage. Accordingly, a plurality of catheters which have been respectively inserted into the plurality of hubs are guided into the one introducer sheath and are introduced into a biological lumen through the lumen in the introducer sheath. For this reason, only one approach site is formed in a person to be treated, and therefore, it is possible to reduce the burden on the person to be treated.

However, the lumen of the introducer sheath is formed to have a size that allows simultaneous insertion of a plurality of catheters, and therefore, it is also necessary to form the outer peripheral portion of the introducer sheath to be large in accordance with the size of the lumen. For this reason, even when using a small number of catheters with respect to the number of catheters which can be inserted into the introducer sheath, and for example, even when using only one catheter, the outer peripheral portion of the introducer sheath has the same size as that when using the set number of catheters. An approach site which is formed in a person to be treated through puncturing is formed in accordance with the size of this introducer sheath. Thus, even when using a small number of catheters, it is necessary to form the approach site having the same size as that when using the set number of catheters. Therefore, there is a disadvantage in that the size of the approach site is formed to be unnecessarily large.

SUMMARY

The disclosure herein provides an introducer sheath which can form an approach site having a size in accordance with the number of catheters to be inserted into a biological lumen and a method for using the same.

Hereinafter, the disclosure will be described using an introducer sheath having two lumens into which two catheters can be simultaneously inserted, as an example.

An introducer sheath for introducing a plurality of catheters into a biological lumen according to the disclosure, includes a sheath main body having a deformation portion which is disposed so as to include at least a part of an outer peripheral portion of the sheath main body; a primary lumen which is formed in the sheath main body; and a secondary lumen which is formed so as to be expandable in the sheath main body, in which the deformation portion is deformed so as to be expanded outwardly in accordance with the expansion of the secondary lumen. With such a configuration, it is possible to change the size of the outer peripheral portion of the introducer sheath in accordance with the number of catheters to be inserted into a blood vessel. Therefore, it is unnecessary to form a larger than necessary approach site in a person to be treated through puncturing, and thus, it is possible to reduce the burden on the person to be treated.

It is preferable that the secondary lumen is formed in the sheath main body in a state of being contracted into a small shape and is expanded by the inner peripheral surface being pressed outwardly. With the formation of the secondary lumen in a sheath main body in a state of being contracted into a small shape, it is possible to reduce the size of the outer peripheral surface of an introducer and to reduce the burden on a person to be treated when inserting the introducer into a blood vessel. In addition, it is possible to expand the secondary lumen with a simple operation, for example, insertion of a dilator, a balloon catheter, or the like into the secondary lumen.

In addition, the deformation portion may be configured so as to be deformed in accordance with the expansion of the secondary lumen and to maintain the expanded state of the secondary lumen. Accordingly, the expanded state of the secondary lumen is maintained even after the pressing for expanding the secondary lumen is released. Therefore, it is easy to introduce a diagnostic device, a therapeutic device, or the like into a lumen in a living body through the introducer sheath.

In addition, the sheath main body has a rigidity portion which is disposed in the vicinity of the primary lumen. The rigidity portion preferably has rigidity so as to maintain a predetermined diameter of the primary lumen. With such a configuration, it is possible to suppress kinking or the like of the introducer during insertion by enhancing the rigidity of the introducer and to suppress the influence of the expansion of the secondary lumen on the size of the diameter of the primary lumen. That is, it is possible to employ a configuration such that only the secondary lumen is deformed without deforming the primary lumen at all times. In such configuration, it is possible to dispose the rigidity portion so as to completely surround the periphery of the primary lumen.

In addition, it is possible to dispose the rigidity portion so as to surround a portion other than a boundary portion between the primary lumen and the secondary lumen, and the boundary portion can thus be deformed so as to be moved into the primary lumen in accordance with the expansion of the secondary lumen.

The deformation portion has a folding portion, which is constituted such that at least a part of the inner peripheral portion of the secondary lumen is folded, and may be deformed so as to be expanded outwardly through release of the folding of the folding portion in accordance with the expansion of the secondary lumen. Accordingly, it is possible to set the maximum diameter during the expansion of the secondary lumen and to prevent the diameter of the secondary lumen from unnecessarily increasing during the expansion.

The deformation portion may be configured such that at least a part of the outer peripheral portion of the sheath main body is folded, and be deformed so as to be expanded outwardly through release of the folding in accordance with the expansion of the secondary lumen. Accordingly, it is possible to set the maximum outer diameter during the expansion of the sheath main body and to suppress an increase in burden on a person to be treated due to an unnecessarily increased outer diameter of the sheath main body during the expansion. In addition, it is possible to reduce the size of the outer peripheral surface of the sheath main body by folding the outer peripheral portion of the sheath main body and to reduce the burden on a person to be treated when inserting the sheath main body into a blood vessel.

In addition, a separation film crossing the inside of the sheath main body may be provided along the sheath main body, and the primary lumen and the secondary lumen may be respectively formed in spaces which are divided by the separation film. The shape of the separation film may be either a linear shape or a curved shape in a cross-sectional portion of the sheath main body, and the primary lumen and the secondary lumen can be formed in the sheath main body with a simple configuration, for example, by provision of the separation film.

In addition, a cylindrical member is disposed along the inner peripheral surface of the sheath main body, the primary lumen is formed in an internal space of the cylindrical member which is disposed along the sheath main body, and the secondary lumen is formed in a space between the inner peripheral surface of the sheath main body and the outer peripheral surface of the cylindrical member. Accordingly, it is easy to set the size of the diameter of the primary lumen and it is possible to form the primary lumen and the secondary lumen with a simple configuration.

A method of using an introducer sheath according to the disclosure herein, includes indwelling the introducer sheath as described above into a biological lumen; introducing a first catheter into the biological lumen through a primary lumen which is formed in a sheath main body; expanding a secondary lumen which is formed so as to be expandable in the sheath main body; deforming a deformation portion, which is disposed so as to include at least a part of the outer peripheral portion of the sheath main body, so as to be expanded outwardly in accordance with the expansion of the secondary lumen; and introducing a second catheter into the biological lumen through the expanded secondary lumen.

According to the disclosure, the deformation portion which is disposed so as to include at least a part of the outer peripheral portion of the sheath main body is deformed so as to be expanded outwardly in accordance with the expansion of the secondary lumen. Therefore, it is possible to form an approach site having a size in accordance with the number of catheters to be inserted into a biological lumen.

BRIEF DESCRIPTION OF THE DRAWINGS

FIG. 7 is a view showing a state in which the secondary lumen of the introducer sheath according to the first exemplary embodiment is expanded.

DETAILED DESCRIPTION

Figure 1:
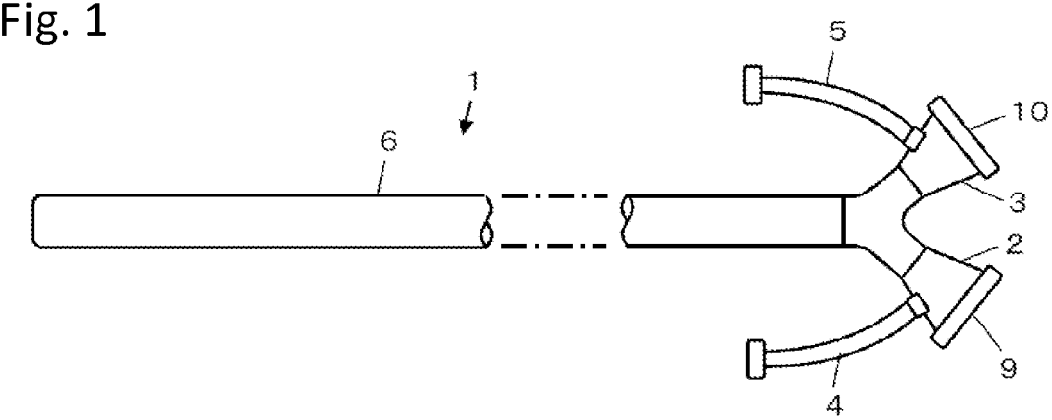
FIG. 1 is a plan view of an introducer sheath according to a first exemplary embodiment of the disclosure.

Hereinafter, embodiments of the disclosure will be described based on the accompanying drawings. Note that, common features are identified by the same reference numerals throughout and so detailed descriptions of already described features will not be repeated. In some cases, dimensional ratios in the drawings are exaggerated and are different from the actual ratios for the convenience of description.

The introducer sheath is a device for securing an access route into a lumen in a living body. Note that, in the description below, the hand operation unit side of the device will be referred to as a "proximal side", and the side through which the device is inserted into the lumen in a living body will be referred to as a "distal side".

FIG. 1 shows an introducer sheath 1 according to a first exemplary embodiment of the disclosure herein. The introducer sheath 1 has a sheath main body 6 for inserting two catheters into a blood vessel; two hubs 2 and 3 which are disposed at a proximal end of the sheath main body 6; and three-way stopcocks 4 and 5 which are provided in the hubs 2 and 3.

Figure 2:
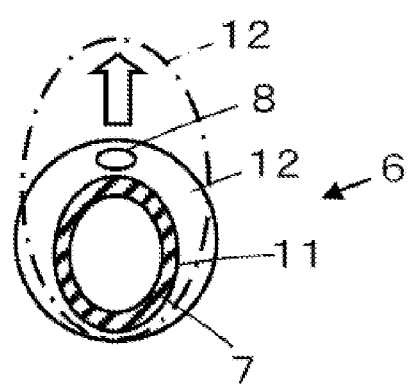
FIG. 2 is a cross-sectional view of a sheath main body of the introducer sheath according to the first exemplary embodiment.

The sheath main body 6 has an elongated shape, and as shown in FIG. 2, a primary lumen 7 and a secondary lumen 8, which extend from a proximal end to a distal end, are formed inside the sheath main body 6.

The primary lumen 7 communicates with a port 9 which is formed in the hub 2, and therefore, it is possible to insert a catheter into the primary lumen 7 by introducing the catheter through the port 9. In addition, the secondary lumen 8 communicates with a port 10 which is formed in the hub 3. In addition, a hemostatic valve (not shown), which is formed of an elastic member is liquid-tightly fixed to the hub 2 and the hub 3, and is configured such that blood does not leak from the port 9 and the port 10 after indwelling an introducer sheath in a blood vessel.

The three-way stopcock 4 is connected to the port 9 of the hub 2, and therefore, it is possible to inject heparin or a physiological salt solution using a syringe or the like and to fill the primary lumen 7 with these solutions. Similarly, a three-way stopcock 5 is connected to the port 10 of the hub 3, and therefore, it is possible to inject heparin or a physiological salt solution into the secondary lumen 8.

Next, the configuration of the sheath main body 6 will be described in detail.

The primary lumen 7 and the secondary lumen 8 are disposed in the sheath main body 6 so as to be adjacent to each other as shown in FIG. 2. The primary lumen 7 has a size that allows insertion of one catheter thereinto, and is formed so as to occupy most of the cross-sectional area in the sheath main body 6. In contrast, the secondary lumen 8 is formed in a state of being contracted into a small shape so as not to affect the size of the outer peripheral portion of the sheath main body 6. For example, the secondary lumen 8 can be formed to have a size small (diameter of about 0.5 mm) enough to pass a guide wire therethrough. In this manner, it is possible to make the outer peripheral portion of the sheath main body 6 have a size approximately the same as that in a case of forming only the primary lumen 7 therein by forming the secondary lumen 8 in a state of being contracted into a small shape.

In addition, a rigidity portion 11 is disposed in the sheath main body 6 so as to completely surround the periphery of the primary lumen 7, and a deformation portion 12 is further disposed so as to cover the rigidity portion 11. The rigidity portion 11 has rigidity so as to support the sheath main body 6 from inside and to maintain a predetermined diameter of the primary lumen 7. Note that the rigidity portion 11 preferably has flexibility to some degree so as to be bent along a blood vessel. The rigidity portion 11 can be formed of, for example, a metal, such as, pseudoelastic alloy, shape memory alloy, and stainless steel, or a resin, such as, polyolefin, polyvinyl chloride, and polyamide.

Figure 3:
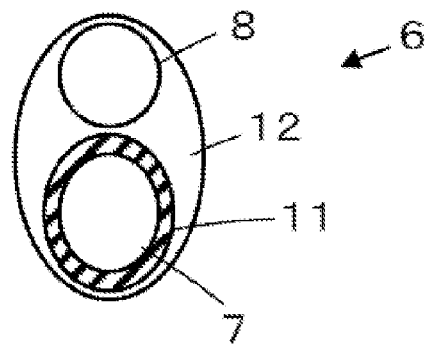
FIG. 3 is a cross-sectional view showing a state in which a secondary lumen of the sheath main body of the introducer sheath according to the first exemplary embodiment is expanded.

In contrast, the deformation portion 12 constitutes the entirety of the outer peripheral portion of the sheath main body 6 and the secondary lumen 8 is disposed inside the deformation portion. The deformation portion 12 is formed to have sufficient flexibility for being deformed in accordance with the expansion of the secondary lumen 8 and slidability between the inner surface of the secondary lumen 8 and the outer surface of a medical instrument, for example, a dilator or a catheter when the medical instrument is inserted into the secondary lumen 8. Accordingly, the secondary lumen 8 is expanded only when a medical instrument is inserted into the secondary lumen 8, and therefore, the burden on a patient decreases. With the insertion of the medical instrument into the secondary lumen 8, the deformation portion 12 is deformed so as to be expanded outwardly as shown in FIG. 2, and accordingly, the outer peripheral portion of the sheath main body 6 is pressed and expanded outwardly. As shown in FIG. 3, the secondary lumen 8 can be expanded until the secondary lumen has a size substantially the same as that of the primary lumen 7. Note that the deformation portion 12 can be formed of a flexible member, for example, natural rubber or synthetic rubber. At this time, a coating may be applied to the inner peripheral surface of the secondary lumen 8 in order to improve the slidability.

Figure 4:
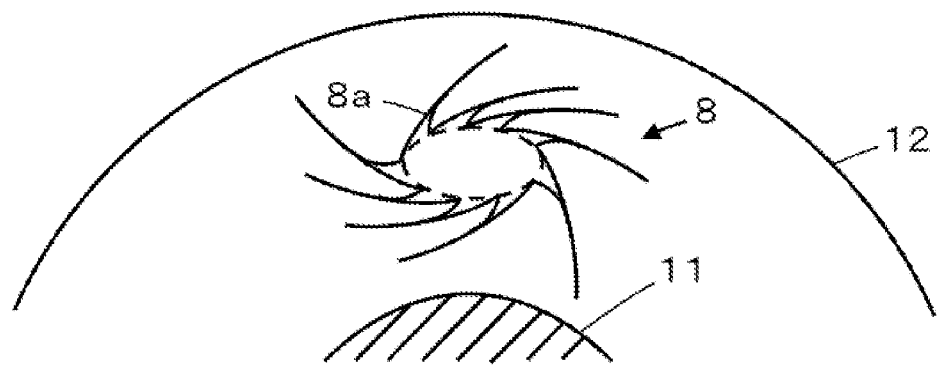
FIG. 4 is a cross-sectional view showing an example of the secondary lumen which is formed in a deformation portion.

The deformation portion 12 may have flexibility for being deformed in accordance with the expansion of the secondary lumen 8 and plasticity for maintaining the expanded state of the secondary lumen 8. Accordingly, the secondary lumen 8 is expanded by the inner peripheral surface being pressed outwardly, and it is possible to maintain the expanded state to some degree even after the pressing is released. The deformation portion 12 is deformed so as to be expanded outwardly in accordance with the expansion of the secondary lumen 8, and accordingly, the outer peripheral portion of the sheath main body 6 is pressed and expanded outwardly. The secondary lumen 8 can be expanded until the secondary lumen has a size substantially the same as that of the primary lumen 7. The deformation portion 12 can have, for example, a folding portion which is configured such that at least a part of the inner peripheral portion of the secondary lumen 8 is folded. Accordingly, the secondary lumen 8 can be formed in the sheath main body in a state of being contracted into a small shape. For example, as shown in FIG. 4, in the deformation portion 12, a plurality of folding portions 8a, which are folded with the inner peripheral surface of the secondary lumen 8 facing the inside, can be formed over the entire periphery of the secondary lumen 8. With such a configuration, it is possible to expand the secondary lumen 8 while releasing the folding of the folding portions 8a due to pressing from the inside by inserting a medical instrument into the secondary lumen 8. In this manner, it is possible to maintain the expanded state of the enlarged secondary lumen 8 to some degree even after the pressing from the inside due to a medical instrument is released. By way of example, the deformation portion 12 can be formed of a synthetic resin, for example, polyolefin, polyvinyl chloride, and polyamide. In addition, even in a case where the deformation portion 12 does not have the folding portions 8a, by disposing a wire having malleability in the deformation portion 12 in the vicinity of the secondary lumen 8 which is expanded by the inner peripheral surface being pressed outwardly, it is possible to maintain the expanded state of the secondary lumen 8 even after the pressing is released.

Next, the operation of exemplary embodiment one will be described.

Figure 5:
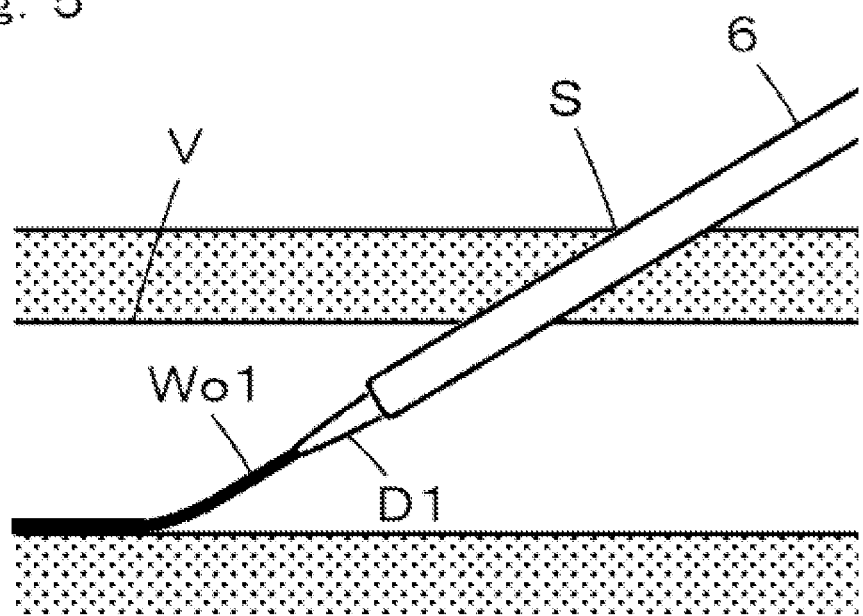
FIG. 5 is a view showing a state in which the introducer sheath according to the first exemplary embodiment is inserted into a blood vessel.

First, only one predetermined site of a person to be treated is punctured to form an approach site S, and a guide wire Wo1 (mini guide wire) is inserted into a blood vessel V through the approach site S. A dilator D1 is inserted into the introducer sheath 1 shown in FIG. 1 through the port 9 which is formed in the hub 2, and a distal portion of the dilator D1 protrudes from a distal end of the introducer sheath 1 through the primary lumen 7. The introducer sheath 1 in which the dilator D1 has been installed in this manner is then inserted into a blood vessel V as shown in FIG. 5 along the guide wire Wo1 which has been previously inserted into the blood vessel V.

Figure 6A:
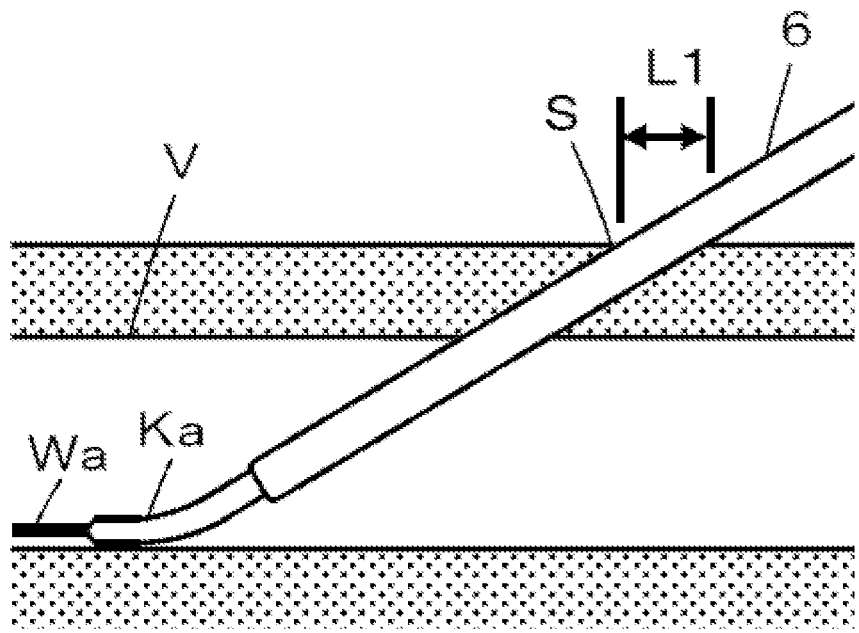
FIG. 6(a) is a view showing a state in which a catheter is introduced into a blood vessel through a primary lumen of the introducer sheath according to the first exemplary embodiment and FIG. 6(b) is a cross-sectional view of the sheath main body of the introducer sheath in the state of FIG. 6(a).
Figure 6B:
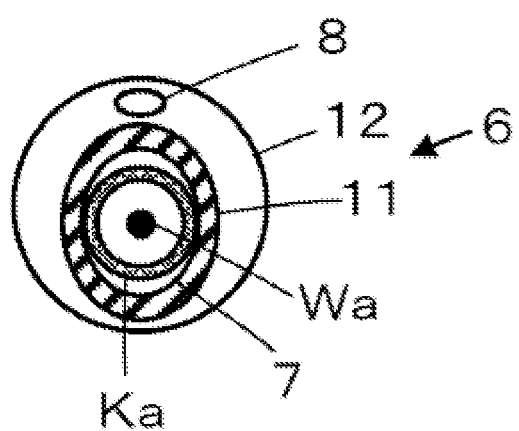

When the introducer sheath 1 is inserted into a predetermined position in the blood vessel V along the guide wire Wo1, the introducer sheath 1 is indwelled in the blood vessel and the dilator D1 and the guide wire Wo1 are pulled out from the introducer sheath 1. Subsequently, another guide wire Wa is introduced through the port 9 of the hub 2 and a distal portion of the guide wire Wa is delivered to the vicinity of a target lesion area. Then, a first catheter Ka is introduced through the port 9 of the hub 2. The introduced first catheter Ka is led out from the distal end of the introducer sheath 1 through the primary lumen 7 as shown in FIGS. 6a and 6b and is inserted into a blood vessel V along the guide wire Wa.

Here, the primary lumen 7 has a size that allows insertion of one catheter, but the secondary lumen 8 maintains a state of being contracted into a small shape so as not to affect the size of the sheath main body 6. For this reason, the outer peripheral portion of the sheath main body 6 has a size substantially the same as that when only the primary lumen 7 is formed therein, that is, a size substantially the same as that of a sheath for inserting one catheter. Accordingly, when inserting only the first catheter Ka into a blood vessel V, it is unnecessary to form a large approach site S into which two catheters are inserted, and it is possible to form the approach site S at a size L1 approximately the same as that when inserting one catheter.

In this manner, it is possible to deliver a distal portion of the first catheter Ka to a target lesion area by inserting the first catheter Ka into the blood vessel V along the guide wire Wa and to treat the lesion area using the first catheter Ka. Note that it is possible to fill the primary lumen 7 by injecting a solution, for example, heparin through the three-way stopcock 4, and thus, it is possible to suppress solidification of blood which has flowed into the primary lumen 7 by filling the primary lumen 7 with heparin.

Subsequently, in a case of treating the lesion area in the blood vessel V using two catheters, a guide wire Wo2 (mini guide wire) is inserted into the secondary lumen 8 of the introducer sheath 1 from the port 10 which has been formed in the hub 3 of the sheath assembly, a dilator D2 is inserted thereinto along the guide wire Wo2, and then, the guide wire Wo2 and the dilator D2 are led out from the distal end of the introducer sheath 1 as shown in FIG. 7. At this time, the dilator D2 is inserted into the introducer sheath 1 while pressing the inner peripheral surface of the sheath main body 6 so as to press and expand the secondary lumen 8. Accordingly, the secondary lumen 8 is expanded so as to have a size substantially the same as that of the primary lumen 7, the deformation portion 12 is deformed so as to be expanded outwardly in accordance with the expansion of the secondary lumen 8, and the outer peripheral portion of the sheath main body 6 is pressed and expanded outwardly. For this reason, the outer peripheral portion of the sheath main body 6 is significantly deformed and the approach site S which has been formed in a person to be treated is also expanded in accordance with the deformation.

Note that the dilator D2 has been used in order to expand the secondary lumen 8. However, an expansion device, for example, a balloon catheter may be used as long as it is possible to expand the secondary lumen 8.

Figure 8A:
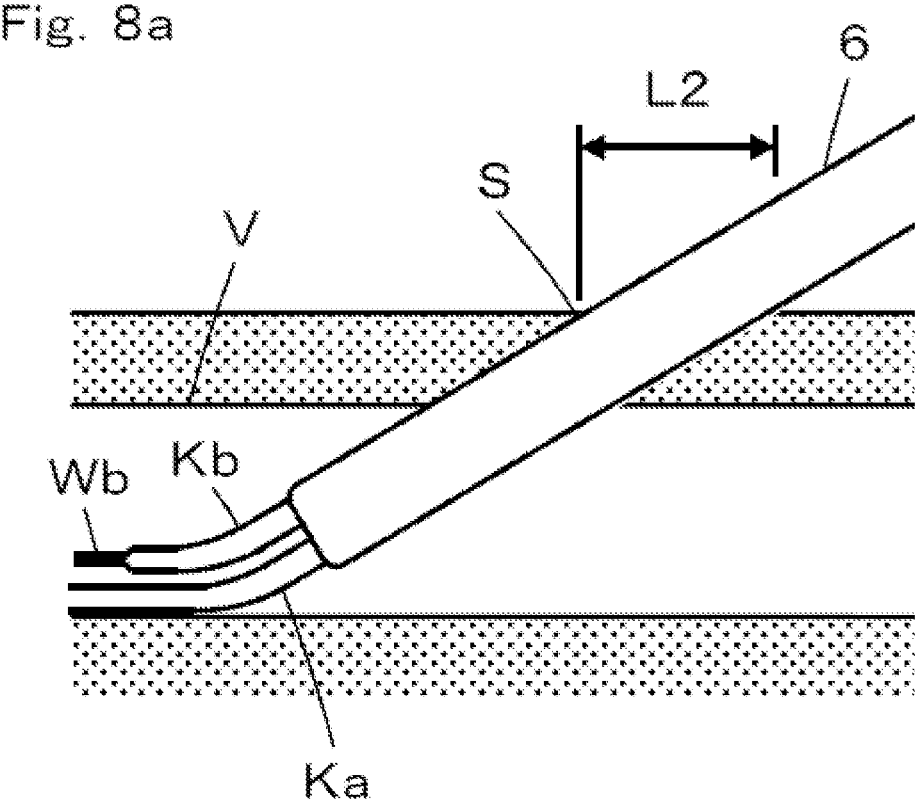
FIG. 8(a) is a view showing a state in which catheters are introduced into a blood vessel through the secondary lumen of the introducer sheath according to, and FIG. 8(b) is a cross-sectional view of the sheath main body of the introducer sheath in the state of FIG. 8(a).
Figure 8B:
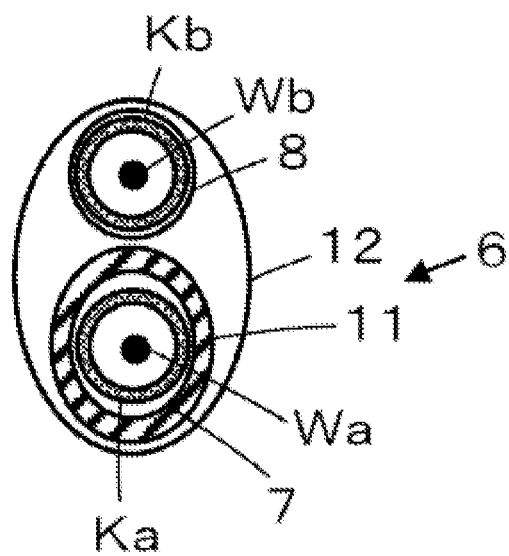

The dilator D2 is pulled out from the inside of the introducer sheath 1 when the secondary lumen 8 in the introducer sheath 1 is expanded in this manner. Then, another guide wire Wb is introduced through the port 10 of the hub 3 and a distal portion of the guide wire Wb is delivered to the vicinity of a target lesion area. Subsequently, a second catheter Kb is introduced through the port 10 of the hub 3. At this time, the secondary lumen 8 is flexible and has high slidability on the inner peripheral surface thereof. Therefore, it is possible to smoothly insert the second catheter Kb even after the dilator D2 is removed. That is, the second catheter Kb which has been introduced through the port 10 of the hub 3 can be smoothly inserted into the secondary lumen 8 without receiving a large amount of pressure from the inner peripheral surface of the deformation portion 12 constituting the secondary lumen 8. In this manner, the second catheter Kb is led out from the distal end of the introducer sheath 1 through the expanded secondary lumen 8 as shown in FIGS. 8a and 8b and is inserted into a blood vessel V along the guide wire Wb.

In this instance, the outer peripheral portion of the introducer sheath 1 is pressed and expanded outwardly by the amount equivalent to the expansion of the secondary lumen 8. Therefore, the size of the outer peripheral portion of the introducer sheath becomes substantially the same as that of a sheath for inserting two catheters without significantly expanding the outer peripheral portion more than necessary. For this reason, the approach site S formed in a person to be treated is formed at a size L2 substantially the same as that when inserting the two catheters, and therefore, it is unnecessary to expand the size larger than the size L2.

In this manner, it is possible to deliver a distal portion of the second catheter Kb to a target lesion area by inserting the second catheter Kb into the blood vessel V along the guide wire Wb and to treat the lesion area using the two catheters of the first catheter Ka and the second catheter Kb. Note that it is possible to suppress solidification of blood which has flowed in terms of the secondary lumen 8 by injecting a solution, for example, heparin through the three-way stopcock 5.

According to the first exemplary embodiment, the size of the outer peripheral portion of the introducer sheath 1 can be changed in accordance with the number of catheters to be inserted into the blood vessel V. For this reason, the approach site S which is formed in a person to be treated through puncturing can be formed to have a size of one catheter when inserting one catheter thereinto and a size of two catheters when inserting two catheters. Therefore, it is unnecessary to form a larger than necessary approach site S, and thus, it is possible to reduce the burden on the person to be treated.

Note that, in the aforesaid exemplary embodiment, the deformation portion 12 is formed so as to constitute the entirety of the outer peripheral portion of the sheath main body 6. However, the deformation portion 12 may be formed to include only a part of the outer peripheral portion of the sheath main body 6 as long as it is possible to expand the outer peripheral portion of the sheath main body 6 outwardly in accordance with the expansion of the secondary lumen 8.

In addition, in the aforesaid exemplary embodiment, one primary lumen 7 and one secondary lumen 8 are formed inside the sheath main body 6. However, a plurality of lumens can be formed in accordance with the number of catheters to be used for treating a lesion area in a blood vessel. For example, a plurality of secondary lumens 8 can be formed with respect to one primary lumen 7.

In addition, in the aforesaid exemplary embodiment, the rigidity portion 11 is disposed so as to completely surround the periphery of the primary lumen 7. However, the disclosure herein is not limited thereto as long as it is possible to maintain the size that allows insertion of the first catheter Ka through the primary lumen 7.

Figure 9A:
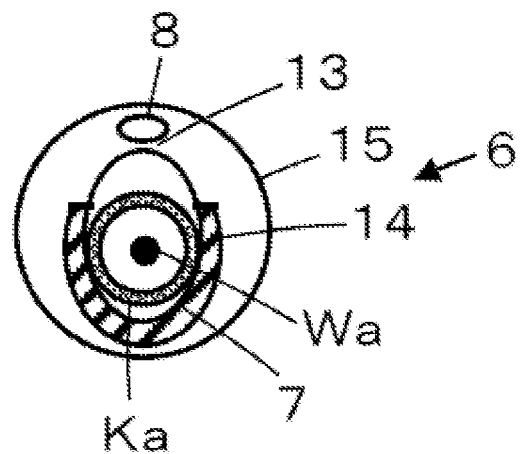
FIG. 9(a) is a cross-sectional view showing a sheath main body of an introducer sheath according to a modification of the first exemplary embodiment in a state in which a catheter is inserted into only a primary lumen and FIG. 9(b) is a cross-sectional view showing a state in which catheters are inserted into the primary lumen and a secondary lumen.
Figure 9B:
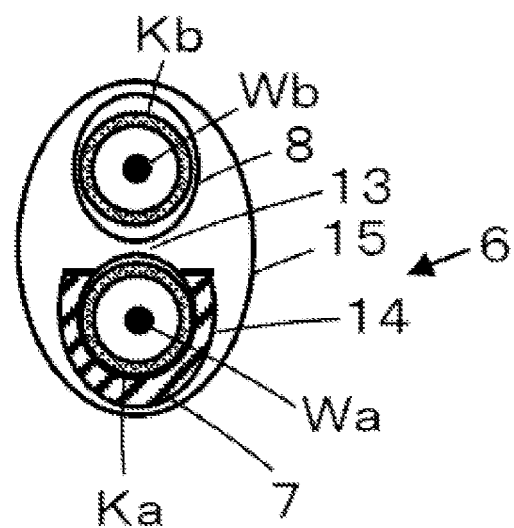

For example, as shown in FIG. 9*a*, it is possible to dispose a rigidity portion 14 along a portion of the periphery of the primary lumen 7, instead of the rigidity portion 11 of the first embodiment, so as to surround a portion which does not include a boundary portion 13 between the primary lumen 7 and the secondary lumen 8. A deformation portion 15 is disposed so as to cover the rigidity portion 14 and to include the boundary portion 13. Accordingly, when the secondary lumen 8 is expanded by inserting a dilator D2 into the secondary lumen, the outer peripheral portion of the sheath main body 6 is deformed so as to be expanded outwardly in accordance with the expansion, and the boundary portion 13 is deformed so as to be moved into the primary lumen 7. That is, the boundary portion 13 is deformed so as to reduce the size of the primary lumen 7 by also being expanded to the primary lumen 7 side while being deformed so as to be expanded outwardly in accordance with the expansion of the secondary lumen 8. As shown in FIG. 9*b*, it is possible to insert the second catheter Kb into the expanded secondary lumen 8 and to insert the second catheter Kb which is led out from the introducer sheath 1 through the secondary lumen 8 into the blood vessel V.

In this manner, the boundary portion 13 is expanded to the primary lumen 7 side as well as the outer peripheral portion of the sheath main body 6 being outwardly expanded in accordance with the expansion of the secondary lumen 8. Therefore, it is possible to further reduce the outer peripheral portion of the introducer sheath 1 when inserting the two catheters. For this reason, it is possible to reduce the size of the approach site S to be formed in a person to be treated and to further reduce the burden on the person to be treated.

In the first exemplary embodiment, the flexible deformation portion 12 which is deformed in accordance with the expansion of the secondary lumen 8 is disposed in the sheath main body 6. However, the disclosure herein is not limited thereto as long as it is possible to expand the outer peripheral portion of the sheath main body 6 outwardly in accordance with the expansion of the secondary lumen 8.

Figure 10A:
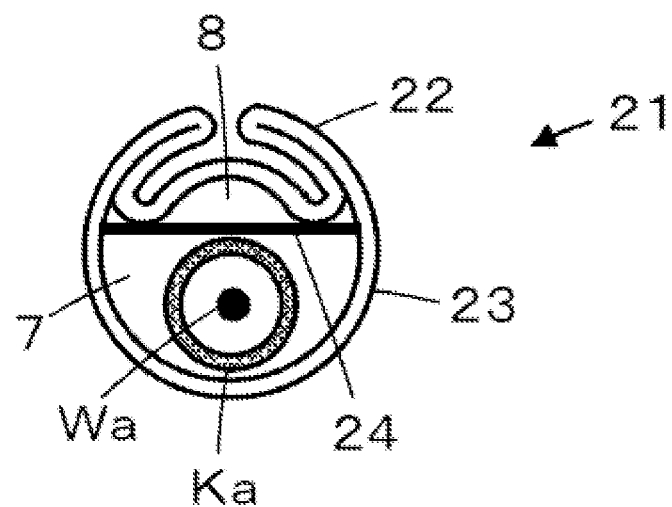
FIG. 10(a) is a cross-sectional view showing a sheath main body of an introducer sheath according to a second exemplary embodiment of the disclosure in a state in which a catheter is inserted into only a primary lumen and FIG. 10(b) is a cross-sectional view showing a state in which catheters are inserted into the primary lumen and a secondary lumen.

For example, as shown in the second exemplary embodiment of FIG. 10*a*, a sheath main body 21 has a deformation portion 22 in which a part of the outer peripheral portion is folded. It is possible to expand the outer peripheral portion of the sheath main body 21 outwardly by releasing the folding of the deformation portion 22 in accordance with the expansion of the secondary lumen 8. Specifically, a rigidity portion 23 is disposed so as to surround the entirety of the outer peripheral portion of the sheath main body 21 and the deformation portion 22 is disposed on a part of the rigidity portion 23. The rigidity portion 23 has rigidity so as to support the sheath main body 21 from outside when inserting the sheath main body 21 into a blood vessel. The rigidity portion can be formed of, for example, a metal, such as, pseudoelastic alloy, shape memory alloy, and stainless steel, or a resin, such as, polyolefin, polyvinyl chloride, and polyamide. Note that the rigidity portion 23 preferably has flexibility to some degree so as to be bent along a blood vessel.

The deformation portion 22 is formed by folding the rigidity portion 23 inwardly so as to overlap the folded portions of the rigidity portion with each other. The overlapping portions of the rigidity portion 23 are bonded to each other such that the folding is held in place. The folding of the deformation portion 22 can be released by disengaging the bonding by pressing the inner peripheral surface of the rigidity portion 23 outwardly with a predetermined amount of pressure.

In addition, a separation film 24 crossing the inside of the rigidity portion 23 is formed along the sheath main body 21 such that the inside is divided by the separation film 24 into the primary lumen 7 and the secondary lumen 8. That is, the primary lumen and the secondary lumen are respectively formed in spaces which are divided by the separation film 24. In a state where the deformation portion 22 is folded, the primary lumen 7 has a size that allows insertion of the first catheter Ka, and is formed so as to occupy most of the inside of the sheath main body 21. In contrast, through the folding of the deformation portion 22, the secondary lumen 8 is formed in a state of being contracted into a small shape so as not to affect the size of the outer peripheral portion of the sheath main body 21. For example, the secondary lumen 8 can be formed to have a size small (diameter of about 0.5 mm) enough to pass a guide wire therethrough.

Note that the size of the primary lumen 7 and the secondary lumen 8 in a state where the folding of the deformation portion 22 is released can be changed depending on the position of the separation film 24. For example, in a cross section of the sheath main body 21, in a case where a linear separation film 24 which passes a middle point of the shape of the cross section thereof is provided, the sizes of the primary lumen 7 and the secondary lumen 8 in the state where the folding is released become substantially the same as each other. Note that the separation film 24 may have enough strength or flexibility to avoid any damage due to insertion of a medical instrument, for example, a dilator or a catheter and can be formed of resin, for example, polyolefin, polyvinyl chloride, and polyamide.

The separation film 24 has enough strength or flexibility to avoid any damage due to expansion of the secondary lumen 8. Therefore, the folding of the deformation portion 22 is released when the inner peripheral surface of the rigidity portion 23 is pressed outwardly with a predetermined amount of pressure by a medical instrument which has been inserted into the secondary lumen 8 and the secondary lumen is then expanded. The deformation portion 22 is deformed so as to be expanded outwardly in accordance with the expansion of the secondary lumen 8 and the outer peripheral portion of the sheath main body 21 is pressed and expanded outwardly. Accordingly, it is possible to press and expand the outer peripheral portion of the sheath main body 21 outwardly in accordance with the expansion of the secondary lumen 8.

Figure 10B:
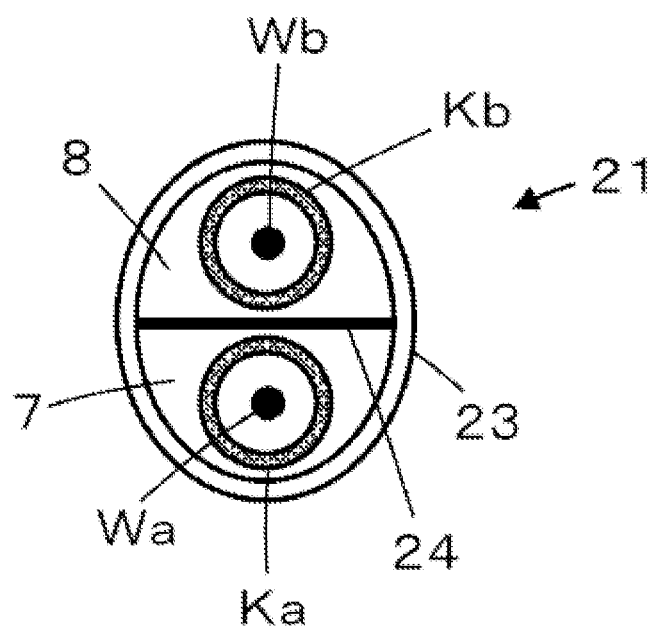

For example, in a cross section of the sheath main body 21, in a case where a linear separation film 24 passes a middle point of the shape of the cross section thereof, as shown in FIG. 10*b*, it is possible to expand the size of the secondary lumen 8 to be substantially the same as that of the primary lumen 7 and to insert the second catheter Kb having the same size as that of the first catheter Ka which is inserted into the primary lumen 7, into the expanded secondary lumen 8.

According to the disclosure herein, it is possible to change the size of the outer peripheral portion of the introducer sheath 1 in accordance with the number of catheters to be inserted into the blood vessel V. Therefore, it is unnecessary to form a large approach site S which is formed in a person to be treated through puncturing, and thus, it is possible to reduce the burden on the person to be treated. In addition, the rigidity portion 23 is disposed so as to surround the entirety of the outer peripheral portion of the sheath main body 21. Therefore, it is possible to improve piercing properties of the introducer sheath 1 and to smoothly insert the introducer sheath 1 into a blood vessel through the approach site S.

Figure 11A:
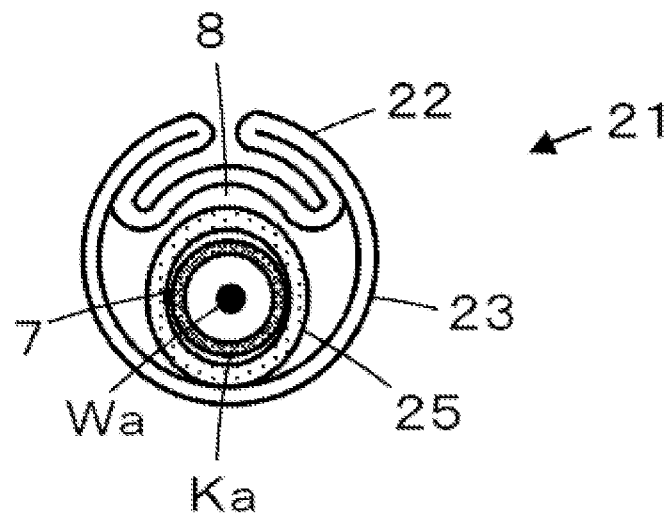
FIG. 11(a) is a cross-sectional view showing a sheath main body of an introducer sheath according to a third exemplary embodiment of the disclosure in a state in which a catheter is inserted into only a primary lumen and FIG. 11(b) is a cross-sectional view showing a state in which catheters are inserted into the primary lumen and a secondary lumen.

In addition, with reference to FIG. 11a, it is possible to configure an introducer sheath which can form two lumens through which catheters can be inserted by expansion of the secondary lumen 8 without using the separation film 24 in the introducer sheath as in the second exemplary embodiment described above.

In FIG. 11a, the separation film 24 is removed from the sheath main body 21 of the second embodiment, and a cylindrical member 25 is provided instead inside the rigidity portion 23 along the inner peripheral surface of the sheath main body 21, and the primary lumen 7 is formed in an internal space of the cylindrical member 25. Moreover, the secondary lumen 8 is formed by a space which can be formed between the outer periphery of the cylindrical member 25 and the inner periphery of the rigidity portion 23.

Figure 11B:
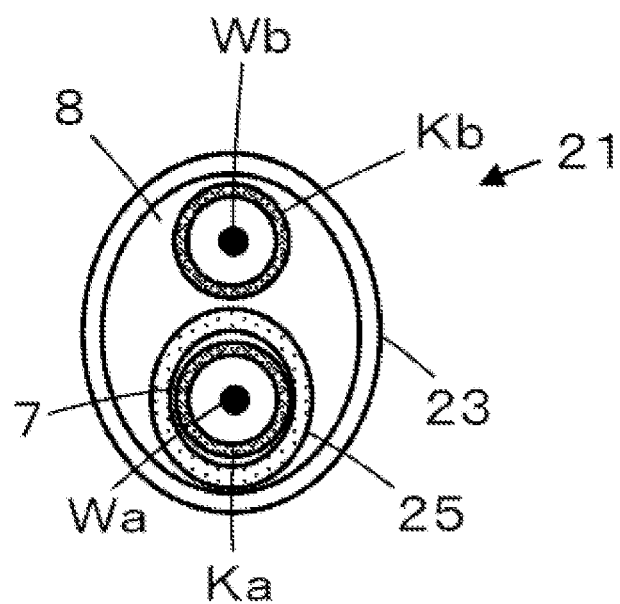

In the third embodiment of FIGS. 11a and 11b, when the deformation portion 22 is in a state of being folded, the rigidity portion 23 is disposed so as to cover the outer periphery of the cylindrical member 25. For this reason, even if the deformation portion 22 is in a state of being folded, the primary lumen 7 has a size that allows insertion of the first catheter Ka, and is formed so as to occupy most of the cross-sectional area in the sheath main body 21. The secondary lumen 8 is formed in a state of being contracted into a small shape so as not to affect the size of the outer peripheral portion of the sheath main body 21, through the folding of the deformation portion 22. For example, the secondary lumen 8 can be formed to have a size small (diameter of about 0.5 mm) enough to pass a guide wire therethrough.

Note that the cylindrical member has enough rigidity to avoid crushing in accordance with the expansion of the secondary lumen 8 and can be formed of, for example, a metal, such as, pseudoelastic alloy, shape memory alloy, and stainless steel, or a resin, such as, polyolefin, polyvinyl chloride, and polyamide. Note that the rigidity portion 23 preferably has flexibility to some degree so as to be bent along a blood vessel.

The cylindrical member has enough rigidity to avoid crushing due to expansion of the secondary lumen 8. Therefore, the folding of the deformation portion 22 is released when the inner peripheral surface of the rigidity portion 23 is pressed outwardly with a predetermined amount of pressure by a medical instrument which has been inserted into the secondary lumen 8 which is then expanded. The deformation portion 22 is deformed as shown in FIG. 11b so as to be expanded outwardly in accordance with the expansion of the secondary lumen 8 and the outer peripheral portion of the sheath main body 21 is pressed and expanded outwardly. Accordingly, it is possible to press and expand the outer peripheral portion of the sheath main body 21 outwardly in accordance with the expansion of the secondary lumen 8.

According to the third exemplary embodiment, similar to the second embodiment, it is possible to change the size of the outer peripheral portion of the introducer sheath 1 in accordance with the number of catheters to be inserted into the blood vessel V. Therefore, it is unnecessary to form an approach site S larger than necessary in a person to be treated through puncturing, and thus, it is possible to reduce the burden on the person to be treated. In addition, the rigidity portion 23 is disposed so as to surround the entirety of the outer peripheral portion of the sheath main body 21. Therefore, it is possible to improve piercing properties of the introducer sheath 1 and to smoothly insert the introducer sheath 1 into a blood vessel through the approach site S.

Note that the rigidity portion 23 of the second and third exemplary embodiments may be configured such that the folding of the deformation portion 22 is released by the inner peripheral surface being pressed outwardly, and can be formed of a material with low rigidity to some degree so as to facilitate the folding of the deformation portion 22.

Note that, in the aforesaid first, second and third embodiments, the introducer sheath 1 is used in order to introduce a catheter into a blood vessel of a person to be treated. However, the introducer sheath can also be used in order to introduce a catheter into biological lumens, for example, bile ducts, trachea, esophagus, and urethra.

The detailed description above describes an introducer sheath and a method of using the same. The disclosure is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An introducer sheath for introducing a plurality of catheters into a biological lumen, comprising:
    a sheath main body having a deformation portion which is disposed so as to include at least a part of an outer peripheral portion of the sheath main body;
    a primary lumen which is formed in the sheath main body;
    a secondary lumen which is formed so as to be expandable in the sheath main body; and
    a rigidity portion surrounding at least a portion of the primary lumen;
    wherein the deformation portion is deformed so as to be expanded outwardly in accordance with the expansion of the secondary lumen;
    wherein the primary lumen possess a predetermined diameter before the expandable secondary lumen is expanded; and
    wherein the deformation portion covers at least a portion of the rigidity portion, the rigidity portion being positioned between the primary lumen and the secondary lumen to thus maintain the predetermined diameter of the primary lumen when the expandable secondary lumen is expanded.

2. The introducer sheath according to claim 1,
    wherein the secondary lumen is formed in the sheath main body in a state of being contracted into a small shape and is expanded by an inner peripheral surface of the secondary lumen being pressed outwardly.

3. The introducer sheath according to claim 1,
    wherein the secondary lumen is formed in the deformation portion which is configured so as to maintain an expanded state of the secondary lumen when being deformed in accordance with the expansion of the secondary lumen.

4. The introducer sheath according to claim 3,
    wherein the deformation portion has a folding portion and at least a part of an inner peripheral portion of the secondary lumen is folded, the deformation portion being deformed so as to be expanded outwardly through release of the folding of the folding portion in accordance with the expansion of the secondary lumen.

5. The introducer sheath according to claim 1,
wherein the deformation portion is configured such that at least a part of the outer peripheral portion of the sheath main body is folded, and the deformation portion is deformed so as to be expanded outwardly through release of the folding in accordance with the expansion of the secondary lumen.

6. The introducer sheath according to claim 5,
wherein the deformation portion is configured so as to be deformed in accordance with the expansion of the secondary lumen and to maintain the expanded state of the secondary lumen.

7. The introducer sheath according to claim 6,
further comprising a separation film crossing inside of the sheath main body, and
wherein the primary lumen and the secondary lumen are respectively formed in spaces which are divided by the separation film.

8. The introducer sheath according to claim 6,
further comprising a cylindrical member disposed along the inner peripheral surface of the sheath main body, and
wherein the primary lumen is formed in an internal space of the cylindrical member and the secondary lumen is formed in a space between the inner peripheral surface of the sheath main body and the outer peripheral surface of the cylindrical member.

9. A method of using an introducer sheath, comprising:
indwelling the introducer sheath according to claim 1 into a biological lumen;
introducing a first catheter into the biological lumen through the primary lumen which is formed in the sheath main body;
expanding the secondary lumen which is formed so as to be expandable in the sheath main body;
deforming the deformation portion, which is disposed so as to include at least a part of the outer peripheral portion of the sheath main body, so as to be expanded outwardly in accordance with the expansion of the secondary lumen; and
introducing a second catheter into the biological lumen through the expanded secondary lumen.

10. The method according to claim 9,
wherein expanding the secondary lumen includes inserting a mechanical instrument into the second lumen.

11. The introducer sheath according to claim 1,
wherein the rigidity portion is separate and distinct from the deformation portion, the rigidity portion formed from a first material, the deformation portion formed from a second material, and the first material being different from the second material.

12. An introducer sheath for introducing a plurality of catheters into a biological lumen, comprising:
a sheath main body configured for insertion of at least two catheters into the biological lumen;
a first hub and a second hub disposed at a proximal end of the sheath main body and forming a first port and a second port, respectively;
a primary lumen formed in the sheath main body, the primary lumen being in fluid communication with the first port;
an expandable secondary lumen formed in the sheath main body, the secondary lumen being in fluid communication with the second port;
a rigidity portion surrounding at least a portion of the primary lumen; and
a deformation portion disposed so as to include at least a part of an outer peripheral portion of the sheath main body and to cover at least a portion of the rigidity portion;
wherein the deformation portion is deformed so as to be expanded outwardly in accordance with the expansion of the secondary lumen;
wherein the primary lumen possess a predetermined diameter before the expandable secondary lumen is expanded; and
wherein the rigidity portion is positioned between the primary lumen and the secondary lumen to maintain the predetermined diameter of the primary lumen when the expandable secondary lumen is expanded.

13. The introducer sheath according to claim 12,
wherein the deformation portion extends on an entirety of the outer peripheral portion of the sheath main body.

14. The introducer sheath according to claim 12,
wherein the rigidity portion surrounds an entirety of the primary lumen.

15. The introducer sheath according to claim 12,
wherein a boundary portion is defined between the primary lumen and the secondary lumen, the rigidity portion surrounding a portion other than the boundary portion.

16. The introducer sheath according to claim 12,
wherein the deformation portion includes a folding portion.

17. The introducer sheath according to claim 12,
further comprising a separation film extending inside of the sheath main body, and
wherein the primary lumen and the secondary lumen are defined in spaces which are divided by the separation film.

18. The introducer sheath according to claim 12,
further comprising a cylindrical member disposed along an inner peripheral surface of the sheath main body, and
wherein the primary lumen is defined in an internal space of the cylindrical member and the secondary lumen is defined in a space between the inner peripheral surface of the sheath main body and an outer peripheral surface of the cylindrical member.

19. The introducer sheath according to claim 12,
wherein the rigidity portion is separate and distinct from the deformation portion, the rigidity portion formed from a first material, the deformation portion formed from a second material, and the first material being different from the second material.

* * * * *